United States Patent [19]

Wijay et al.

[11] Patent Number: 5,066,282
[45] Date of Patent: Nov. 19, 1991

[54] POSITIVE DISPLACEMENT PISTON DRIVEN BLOOD PUMP

[75] Inventors: Bandula Wijay, Webster; Paolo Angelini, Houston, both of Tex.

[73] Assignee: Leocor, Inc., Houston, Tex.

[21] Appl. No.: 347,406

[22] Filed: May 4, 1989

Related U.S. Application Data

[63] Continuation-in-part of Ser. No. 100,363, Sep. 23, 1987, Pat. No. 4,921,483, which is a continuation-in-part of Ser. No. 811,162, Dec. 19, 1985, abandoned, said Ser. No. 100,363, is a continuation-in-part of Ser. No. 303,544, Jan. 27, 1989, abandoned, which is a continuation-in-part of Ser. No. 303,550, Jan. 27, 1989, abandoned.

[51] Int. Cl.$^5$ .............................................. A61M 1/00
[52] U.S. Cl. ..................................... 604/152; 604/153; 604/247; 128/DIG. 12
[58] Field of Search ............... 604/151, 152, 153, 154, 604/155, 141, 142, 246, 247; 417/437, 540; 128/DIG. 12

[56] References Cited

U.S. PATENT DOCUMENTS

| | | | |
|---|---|---|---|
| 3,298,320 | 1/1967 | Latham | 604/153 |
| 3,447,479 | 6/1969 | Rosenberg | 604/152 X |
| 4,634,430 | 1/1987 | Polaschegg | 128/DIG. 12 X |
| 4,857,054 | 8/1989 | Helfer | 604/102 |

OTHER PUBLICATIONS

"Myocardial Salvage Prior to Emergency Coronary Bypass Surgery for PTCA-Induced Coronary Occlusion", Ulrich W. Busch, M.D., Ulrich Pfeiffer, M.D., Richard Bauer, M.D., Ph.D., Ulrich Renner, M.D., Rudolf Babic, M.D., Gunther Flumel, M.D., and Hans Blomer, M.D. from The Texas Heart Institute Journal, pp. 113-122, vol. 13, No. 1, Mar. 1986.

*Primary Examiner*—C. Fred Rosenbaum
*Assistant Examiner*—Corrine Maglione
*Attorney, Agent, or Firm*—Rosenblatt & Associates

[57] ABSTRACT

The invention is a disposable, positive-displacement piston pump, having a polycarbonate body, a piston, an inlet valve, and an outlet valve. The outlet valve is connected to an exit chamber, which is separated from the exit valve by an elastomeric membrane. The elastomeric membrane encloses an accumulation chamber which is filled with a fluid such as air under atmospheric pressure. Pulsations in outlet pressure caused by stroking of the piston are dampened by the flexing action of the elastomeric membrane, compressing the fluid within the accumulator chamber. The throw out of the pump is pressure-dampened and is of sufficient pressure to flow through very low-profile angioplasty catheters having perfusion lumens extending therethrough. The combination of the pump with a very low-profile balloon angioplasty catheter allows access of the catheter to a constricted passage with the ability to pump a sufficient volume of blood through such a low-profile catheter during balloon inflations.

25 Claims, 2 Drawing Sheets

POSITIVE DISPLACEMENT PISTON DRIVEN BLOOD PUMP

This application is a C.I.P. of U.S. Ser. No. 7/100,363 filed Sept. 23, 1987, now Pat. No. 4,921,483, entitled "Angioplasty Catheter", which has two divisional applications: U.S. Ser. No. 07/303,544 filed Jan. 27, 1989, now abandoned, entitled "Angioplasty Catheter" and U.S. Ser. No. 07/303,550 filed Jan. 27, 1989, now abandoned, entitled "Angioplasty Catheter". U.S. Ser. No. 07/100,363 is a C.I.P. of U.S. Ser. No. 811,162 filed Dec. 19, 1985, entitled "Angioplasty Catheter", which is abandoned. The contents of all said applications are incorporated by reference as if fully set forth herein.

FIELD OF THE INVENTION

The invention relates to the field of equipment for elevating the pressure of blood to use during surgery or coronary angioplasty procedures.

BACKGROUND OF THE INVENTION

Recently, balloon angioplasty procedures have become more prevalent as a way of treating stenosis in arteries in a patient's body. It has also been desirable to provide catheters having as low a profile as possible to reach as far as possible into the most constricted of passages. It is also desirable to continue the flow of blood during inflation of the balloon to prevent ischemia, which may ensue during protracted inflations of the balloon.

The efforts to reduce the profile of catheters has resulted in smaller and smaller lumens within such catheters which are capable of transporting blood through its distal end during balloon inflation. As a result, higher and higher pressures have been needed to push the requisite amount of blood through lumens having reduced cross-sectional areas.

The concept of pumping blood during balloon inflation incorporating a pump was originally described in an earlier U.S. application Ser. No. 100,363, filed Sept. 23, 1987, invented by Bandula Wijay and Paolo Angelini.

In the past, peristaltic pumps have been used to pump blood. These pumps suffer from two disadvantages. First, their ability to develop output pressure is limited, as compared to the pump of the present invention, which is capable of generating pressures to about 300 psig. Secondly, the tube used in peristaltic pumps can suffer from partial disintegration, resulting in a release of particulates into the bloodstream, having undesirable effects.

Not only is it important to pump a specified volume per unit of time through a catheter during coronary angioplasty, but it is also important to be able to get a good idea of the pressures developed by the pump, which can also be used as a means of determining the blood flow rates.

Ordinarily, a positive displacement pump, such as a piston pump, would create pressure pulses with every stroke. The apparatus of the present invention provides a pulsation-dampening mechanism with the pump to smooth out pressure pulses, thereby allowing continuous blood flow as well as precise flow measurements to be possible during balloon inflation. The pump can be built from materials that allow the body, including the pulsation-dampening feature, to be disposable. The pump body can be used in combination with a motor and a drive, with the motor and drive being reusable with each disposable pump body. The pump body of the present invention can also operate in any position and is small enough so that it can be used in emergency situations, such as emergency bypass graft surgery, to keep the patient's heart supplied with blood.

Pulsation dampeners have been in use with generally multi-cylinder piston pumps in the oil and gas business to pump a variety of well fluids as a means of reducing pipe vibration at the pump discharge.

Piston pumps have been employed to pump saline and other medications through intravenous catheters.

Peristaltic pumps have been in use for pumping blood during open-heart surgery to perfuse coronary arteries. Peristaltic pumps are very low-pressure pumps; i.e., 80–120 psig maximum. Peristaltic pumps experience slippage and do not deliver a volumetrically reliable flow. The advent of smaller and smaller angioplasty catheters has made it necessary to develop greater blood pressures to be able to pump a sufficient volume through smaller and smaller catheters during PTCA. The pump of the present invention meets this need.

SUMMARY OF THE INVENTION

The invention is a disposable, positive-displacement piston pump, having a polycarbonate body, a piston, an inlet valve, and an outlet valve. The outlet valve is connected to an exit chamber, which is separated from the exit valve by an elastomeric membrane. The elastomeric membrane encloses an accumulation chamber which is filled with a fluid such as air under atmospheric pressure. Pulsations in outlet pressure caused by stroking of the piston are dampened by the flexing action of the elastomeric membrane, compressing the fluid within the accumulator chamber. The output of the pump is pressure-dampened and is of sufficient pressure to flow through very low-profile angioplasty catheters having perfusion lumens extending therethrough. The combination of the pump with a very low-profile balloon angioplasty catheter allows access of the catheter to a constricted passage with the ability to pump a sufficient volume of blood through such a low-profile catheter during balloon inflations, while at the same time significantly eliminating pressure pulsations with each stroke.

DETAILED DESCRIPTION OF THE PREFERRED EMBODIMENT

Figure 1:
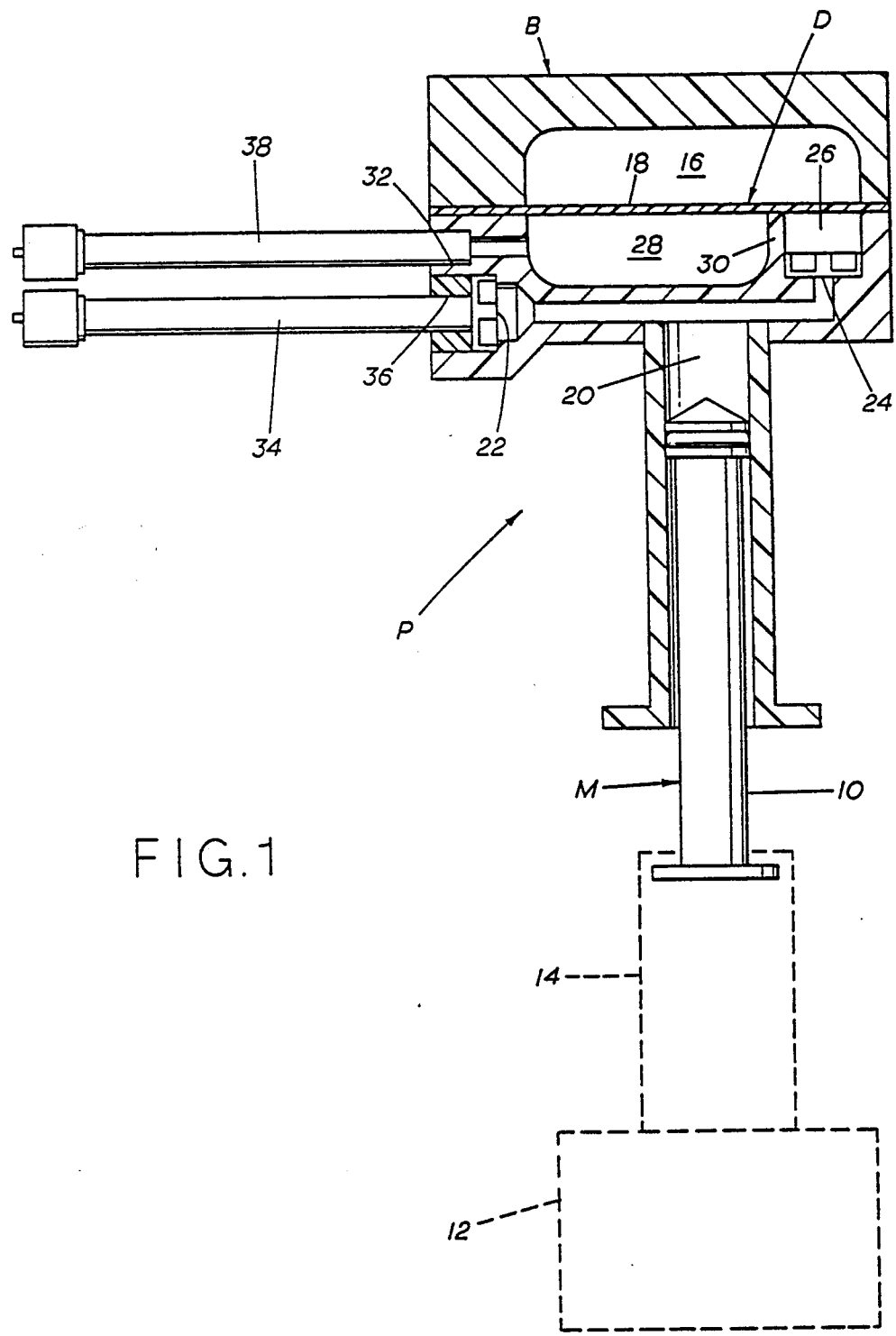
FIG. 1 is a sectional schematic view of the pump, showing its operating components.

As shown in FIG. 1, the pump P includes a body B. The pump P includes means for elevating pressure M, which further comprises of a plunger 10, a drive motor 12, and a linkage 14. Operation of the motor 12 results in oscillatory movement of the plunger 10.

As shown in FIG. 1, the body B further includes pulsation-dampening means D, which further comprises of an accumulator cavity 16 and a flexible membrane 18 made preferably of polyurethane having a Shore hardness of 60A to 55D. Other materials and hardnesses can be used without departing from the spirit of the invention. While FIG. 1 shows the pulsation-dampening means D integral with body B, pulsation-dampening means D can be made separable from body B without departing from the spirit of the invention.

The pump P also includes a pressurization chamber 20. The plunger 10 reciprocates within pressurization chamber 20. Inlet valve 22 and outlet valve 24 are in flow communication with pressurization chamber 20.

When plunger 10 moves in the direction to expand the volume of pressurization chamber 20, such movement draws open valve 22 and draws closed valve 24, thereby filling pressurization chamber 20 with blood. Conversely, when plunger 10 moves in the opposite direction, valve 22 is urged into the closed position and valve 24 is opened. Blood then flows through valve 24 into exit port 26. The flow of blood into exit port 26 builds up the pressure therein and displaces flexible membrane 18, thereby compressing the fluid in accumulator cavity 16 and allowing flow communication between exit port 26 and exit chamber cavity 28. Cavity 16 can be full of air at atmospheric pressure. Other fluids and/or initial chamber pressures higher than atmospheric can be used without departing from the invention. Conversely, when the pump is on the intake stroke and valve 24 is closed, flexible membrane 18 completely covers exit chamber cavity 28, as well as exit port 26, and prevents flow between those two regions. This occurs because flexible membrane 18 seats up against wall 30.

After the blood passes into exit chamber cavity 28, it passes through outlet opening 32. Inlet tube 34 may be connected to inlet port 36, and outlet tube 38 may be connected to outlet opening 32.

The preferred material for body B is polycarbonate, although other materials can be used without departing from the spirit of the invention. It is preferred that the material of body B be transparent so that if there are any gas bubbles in the blood it can readily be seen. Additionally, a transparent body B allows rapid examination of the condition of flexible membrane 18.

The drive mechanism 14 can be preferably a reversible ball screw type of drive, but other drives resulting in oscillatory movement can be used without departing from the spirit of the invention.

Figure 2:
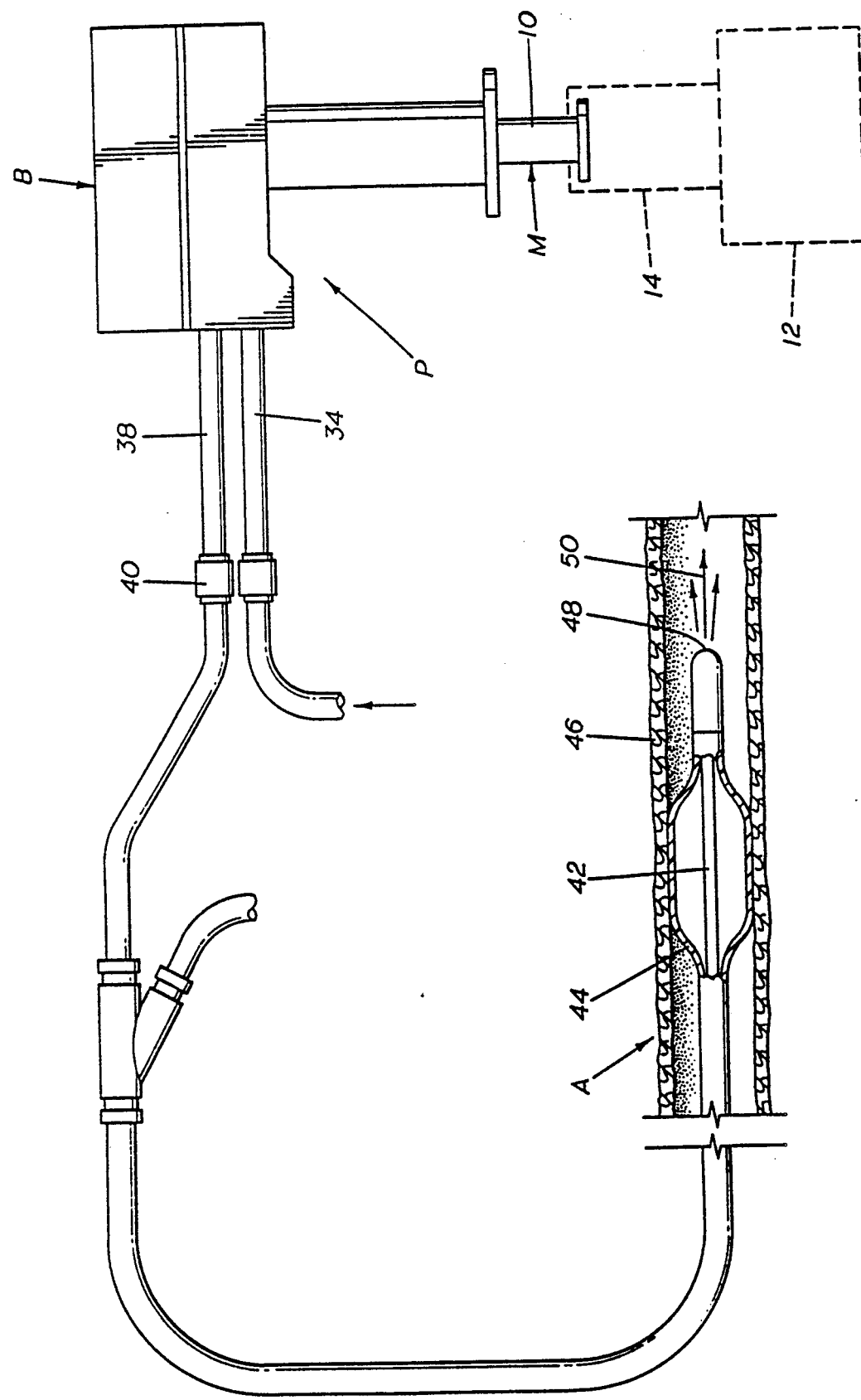
FIG. 2 shows the combination of the pump of FIG. 1 with an angioplasty balloon catheter as it is used within the patient and illustrating how the pump pushes blood through the catheter during balloon inflation.

As seen in FIG. 2, the outlet tube 38 can be connected to a fitting 40 on an angioplasty catheter A. The angioplasty catheter A has a lumen 42 extending therethrough and a balloon 44, which when inflated as shown in FIG. 2, cuts off the blood flow in the artery 46. When the pump P is operated, blood is drawn from a blood supply, such as a blood bag or directly or indirectly from the patient, such as from a renal vein or artery. The blood moves into inlet tube 34, through the pump and into outlet tube 38, through the lumen 42 of angioplasty catheter A, and out the distal end 48. With the pump operating, the blood 50 passes through the distal end 48 of angioplasty catheter A. Accordingly, with the blood 50 flowing in artery 46 during expansion of balloon 44, the onset of ischemia is less likely. The use of the pump P permits greater blood pressures to be developed so that lower profile angioplasty catheters A can be used with lumens 42 having smaller diameters, but at the same time a sufficient flow of blood can be pumped through the angioplasty catheter A to the distal end 48.

The pump P of the present invention is portable and can be operated in any position. It is small, about 1—$\frac{1}{2}$"×4—$\frac{1}{2}$"×3—$\frac{1}{2}$". The driver is about 4"×3"×10". The combined assembly is easily transported and is lightweight. After use, the pump section can be disposed of and the drive motor and linkage, 12 and 14 respectively, can be reused with another sterile pump.

The addition of the accumulator cavity 16, coupled with the flexible membrane 18, smoothes out the pressure pulses to allow more accurate flow and pressure measurements, which can be accomplished by adding the appropriate instruments in the outlet tube 38 or between tube 38 and fitting 40.

Alternatively, chamber 20 and plunger 10 can be configured in a double-acting arrangement, not shown, so that blood is pumped regardless of which way the plunger 10 strokes. This configuration reduces pulsation and may be used with or without pulsation dampening means D.

The foregoing disclosure and description of the invention are illustrative and explanatory thereof, and various changes in the size, shape and materials, as well as in the details of the illustrated construction, may be made without departing from the spirit of the invention.

What is claimed is:

1. A pumping source for pumping blood comprising:
   a pump body;
   means on said body for elevating pressure of blood passing through said body; and
   means in flow communication with said body for dampening pulsation of the blood as it emerges from said pump body, said pulsation dampening means further comprising:
   a housing defining an accumulator cavity therein; and
   a membrane covering said accumulator cavity, thereby isolating blood passing through said body from said cavity.

2. The pump of claim 1 wherein said pulsation-dampening means is integral with said pump body and wherein said membrane is disposed in said pulsation dampening means in a manner as to avoid the creation of dead spots where blood can accumulate in the flowpath through said body.

3. The pump of claim 1 wherein said pressure-elevating means further comprises:
   at least one inlet valve;
   at least one outlet valve;
   at least one pressurization chamber defining a volume in fluid communication with both said inlet and outlet valves; and
   means for varying the volume of said pressurization chamber.

4. The pumping system of claim 3 wherein:
   said pressurization chamber is cylindrical; and
   said volume-varying means is a piston.

5. The pumping system of claim 1, further comprising:
   a balloon angioplasty catheter having a perfusion lumen having an internal diameter adjacent its distal end of approximately 0.020 inches extending therethrough; and
   said body in flow communication with said perfusion lumen in said catheter, thereby allowing pulsation-dampened, pressurized blood to be pumped through the catheter during balloon angioplasty procedures.

6. The apparatus of claim 1 wherein said pump further comprises:
   drive means connected to said pressure-elevating means for selective operation thereof;
   said pump, including said driver, is portable.

7. The apparatus of claim 6 wherein:

said body, pressure-elevating means and pulsation-dampening means are disposable and said drive means is reusable with replacement units comprising a body, pressure-elevating means and pulsation-dampening means.

8. An apparatus for perfusing blood during angioplasty comprising:
a blood pump capable of developing pressure of at least 120 psig;
means in flow communication with said pump for dampening pulsation of the blood as it emerges from said pump, said pulsation dampening means further comprising:
a housing defining an accumulator cavity therein; and
a membrane covering said accumulator cavity, thereby isolating blood passing through said body from said cavity;
an angioplasty catheter having a perfusion lumen, having an internal diameter adjacent its distal end of approximately 0.020 inches, running through it;
said pump in flow communication with said perfusion lumen to allow blood to be pumped through said lumen and distally of the catheter when said catheter is used on a patient.

9. The apparatus of claim 8 wherein said pump further comprises an inlet port adapted to be mounted to a patient's renal vein or an artery, thereby allowing continuous blood flow from the patient through said pump and said catheter during angioplasty.

10. The apparatus of claim 8 wherein said pump further comprises:
drive means connected to said pump for selective operation thereof;
said pump, including said driver, is portable.

11. The apparatus of claim 10 where said pump is disposable and said drive means can be used with replacement pumps.

12. The pump of claim 8 wherein said pulsation-dampening means is integral with said body and wherein said membrane is disposed in said pulsating dampening means in a manner as to avoid the creation of dead spots where blood can accumulate in the flow-path through said body.

13. A pumping source for pumping blood comprising:
a pump body;
means on said body for elevating pressure of blood passing through said body; and
means in flow communication with said body for dampening potation of the blood as it emerges from said pump body, said pulsation dampening means further comprising:
a housing defining an accumulator cavity therein; and
a membrane covering said accumulator cavity, thereby isolating blood passing through said body from said cavity;
at least one inlet valve;
at least one outlet valve;
a least one pressurization chamber defining a volume in fluid communication with both said inlet and outlet valves; and
means for varying the volume of said pressurization chamber;
said outlet valve is in flow communication with an exit port in said body;
said membrane covering said exit port when said outlet valve is in the closed position, said accumulator cavity disposed on the opposite side of said membrane from said exit port;
said body further comprising an exit chamber cavity defined therein, said exit chamber cavity spaced apart from said exit port;
said exit chamber cavity is in flow communication with said exit port when said outlet valve is open and said membrane flexes, thereby reducing the volume of said accumulator cavity.

14. The pumping system of claim 13 wherein said body further comprises an outlet opening in flow communication with said exit chamber cavity.

15. The pumping system of claim 14, further comprising:
a balloon angioplasty catheter having a perfusion lumen having an internal diameter adjacent its distal end of approximately 0.020 inches extending therethrough; and
said outlet opening in said body in flow communication with said perfusion lumen in said catheter, thereby allowing pulsation-dampened, pressurized blood to be pumped through the catheter during balloon angioplasty procedures.

16. The pumping system of claim 15 wherein said pulsation-dampening means is integral with said body and wherein said membrane is disposed in said pulsating dampening means in a manner as to avoid the creation of dead spots where blood can accumulate in the flow-path through said body.

17. A blood pump comprising:
a body defining a cavity therein;
at least one double-acting piston dividing said cavity into at least one first and second chambers;
inlet and outlet valves in flow communication with said first and second chambers;
said valves selectively operable in response to movement of said piston to allow sequential operation of said valves to facilitate pressurization of blood in said first chamber as said piston moves in one direction, then in said second chamber as said piston moves in an opposite direction;
means in said body for dampening pulsation of the pressure of the blood as it emerges from pump, said pulsation-dampening means further comprising:
a housing defining an accumulator cavity therein; and
a membrane covering said accumulator cavity, thereby isolating blood passing through said body from said cavity.

18. The pump of claim 17 wherein said pulsation-dampening means is integral with said body and wherein said membrane is disposed in said pulsation dampening means in a manner as to avoid the creation of dead spots where blood can accumulate in the flow-path through said body.

19. A pumping source for pumping blood comprising:
a pump body;
means on said body for elevating pressure of blood passing through said body; and
means in flow communication with said body for dampening pulsation of the blood as it emerges from said pump body, said pulsation dampening means further comprising:
a housing defining an accumulator cavity therein; and
a membrane covering said accumulator cavity, thereby isolating blood passing through said body from said cavity;
a balloon angioplasty catheter having a perfusion lumen having an internal diameter adjacent its distal end of approximately 0.020 inches extending therethrough; and said body in flow communication with said perfusion lumen in said catheter, thereby allowing pulsation-dampened, pressurized blood to be pumped through the catheter during balloon angioplasty procedures;

said pressure-elevating means further comprises an inlet port adapted to be mounted to a patient's renal vein or an artery, thereby allowing continuous blood flow from the patient through said pump and said catheter during angioplasty.

20. A pumping source for pumping blood comprising:
a pump body;
means on said body for elevating pressure of blood passing through said body; and
means in flow communication with said body for dampening pulsation of the blood as it emerges from said pump body, said pulsation dampening means further comprising:
a housing defining an accumulator cavity therein; and
a membrane covering said accumulator cavity, thereby isolating blood passing through said body from said cavity;
said pressure-elevating means is capable of developing pressures at least as large as 120 psig.

21. A pumping source for pumping blood comprising:
a pump body;
means on said body for elevating pressure of blood passing through said body; and
means in flow communication with said body for dampening pulsation of the blood as it emerges form said pump body, said pulsation dampening means further comprising:
a housing defining an accumulator cavity therein; and
a membrane covering said accumulator cavity, thereby isolating blood passing through said body from said cavity;
a balloon angioplasty catheter having a perfusion lumen having an internal diameter adjacent its distal end of approximately 0.020 inches extending therethrough; and
said body in flow communication with said perfusion lumen in said catheter, thereby allowing pulsation-dampened, pressurized blood to be pumped through the catheter during balloon angioplasty procedures;
said pressure-elevating means is capable of developing pressures at least as large as 120 psig.

22. A blood pump comprising:
a body defining a cavity therein;
at least one double-acting piston dividing said cavity into at least one first and second chambers;
inlet and outlet valves in flow communication with said first and second chambers;
said valves selectively operable in response to movement of said piston to allow sequential operation of said valves to facilitate pressurization of blood in said first chamber as said piston moves in one direction, then in said second chamber as said piston moves in an opposite direction;
said pump is capable of developing pressure at least as large as 120 psig.

23. A pumping source for pumping blood comprising:
a pump body;
means on said body for elevating pressure of blood passing through said body; and
means in flow communication with said body for dampening pulsation of the blood as it emerges from said pump body, said pulsation dampening means further comprising:
a housing defining an accumulator cavity therein; and
a membrane covering said accumulator cavity, thereby isolating blood passing through said body from said cavity;
a balloon angioplasty catheter having a perfusion lumen having an internal diameter adjacent its distal end of approximately 0.020 inches extending therethrough; and
said body in flow communication with said perfusion lumen in said catheter, thereby allowing pulsation-dampened, pressurized blood to be pumped through the catheter during balloon angioplasty procedures;
said pump further comprises:
drive means connected to said pressure-elevating means for selective operation thereof;
said pump, including said driver, is portable.

24. The apparatus of claim 23 wherein:
said body, pressure-elevating means and pulsation-dampening means are disposable and said drive means is reusable with replacement units comprising a body, pressure-elevating means and pulsation-dampening means.

25. A blood pump comprising:
a body defining a cavity therein;
at least one double-acting piston dividing said cavity into at least one first and second chambers;
inlet and outlet valves in flow communication with said first and second chambers;
said valves selectively operable in response to movement of said piston to allow sequential operation of said valves to facilitate pressurization of blood in said first chamber as said piston moves in one direction, then in said second chamber as said piston moves in an opposite direction;
means in said body for dampening pulsation of the pressure of the blood as it emerges from pump, said pulsation-dampening means further comprising:
a housing defining an accumulator cavity therein; and
a membrane covering said accumulator cavity, thereby enclosing said cavity;
said pulsation-dampening means is integral with said body and wherein said membrane is disposed in said pulsation dampening means in a manner as to avoid the creation of dead spots where blood can accumulate in the flowpath through said body.

* * * * *